(12) United States Patent
Doyle (10) Patent No.: US 12,225,955 B2
(45) Date of Patent: Feb. 18, 2025

(54) SYSTEM FOR MOLECULAR IMPRINTED PROTECTIVE FACE MASK

(71) Applicant: Utah Valley University, Orem, UT (US)

(72) Inventor: Timothy Edwin Doyle, Orem, UT (US)

(73) Assignee: Utah Valley University, Orem, UT (US)

( * ) Notice: Subject to any disclaimer, the term of this patent is extended or adjusted under 35 U.S.C. 154(b) by 904 days.

(21) Appl. No.: 16/917,469

(22) Filed: Jun. 30, 2020

(65) Prior Publication Data

US 2021/0386142 A1  Dec. 16, 2021

Related U.S. Application Data

(63) Continuation-in-part of application No. 16/900,682, filed on Jun. 12, 2020.

(51) Int. Cl.
*B01L 3/00* (2006.01)
*A41D 13/11* (2006.01)
(Continued)

(52) U.S. Cl.
CPC .......... *A41D 13/1192* (2013.01); *A61B 5/082* (2013.01); *A61B 5/1468* (2013.01);
(Continued)

(58) Field of Classification Search
CPC ........ A61M 16/105; A61M 2205/3303; A61M 2205/7536; A61M 15/0085; A61M 2205/0238; A61M 2230/437; A61M 2205/7509; A61M 2205/7518; A61M 15/02; A62B 23/025; A62B 9/006; A62B 18/025; A62B 18/02; A62B 23/02; B01D 39/1692; B01D 39/04; B01D 2239/0421; B01D 2239/0492; B01D 2239/0636; B01D 39/1623; B01D 2239/0414; B01D 2239/0478; B01D 39/1676;
(Continued)

(56) References Cited

U.S. PATENT DOCUMENTS 5,070,243 A   12/1991   Bornstein et al.
8,357,275 B2   1/2013   Vanaja et al.
(Continued)

FOREIGN PATENT DOCUMENTS

WO   2008116165 A2   9/2008

OTHER PUBLICATIONS

U.S. Appl. No. 16/900,682, "Office Action Summary", USPTO, Aug. 9, 2023, pp. 1-51.
(Continued)

*Primary Examiner* — Jennifer Wecker
*Assistant Examiner* — Oyeleye Alexander Alabi
(74) *Attorney, Agent, or Firm* — Kunzler Bean & Adamson (57) ABSTRACT

Disclosed herein is a molecular imprinted protective face mask comprising a supportive structure, a surface material that receives and retains a molecular imprint and that is positioned to contact airborne molecules during use, a molecular imprint of a bioactive molecule wherein an imprinted cavity is at least one of a bioactive molecule with a molecular configuration that captures a specific airborne and/or microdroplet-borne molecule and a protein with a binding site that captures a specific molecule.

21 Claims, 8 Drawing Sheets

100

(51) Int. Cl.

| | |
|---|---|
| *A61B 5/00* | (2006.01) |
| *A61B 5/08* | (2006.01) |
| *A61B 5/1468* | (2006.01) |
| *A61B 5/1477* | (2006.01) |
| *A61L 2/03* | (2006.01) |
| *A61L 2/10* | (2006.01) |
| *A61L 2/26* | (2006.01) |
| *A61M 15/02* | (2006.01) |
| *A61M 16/10* | (2006.01) |
| *A62B 18/02* | (2006.01) |
| *A62B 23/02* | (2006.01) |
| *B01D 39/16* | (2006.01) |
| *B01F 23/00* | (2022.01) |
| *B01F 23/41* | (2022.01) |
| *B01F 101/23* | (2022.01) |
| *B23Q 17/24* | (2006.01) |
| *C07K 14/705* | (2006.01) |
| *C12M 1/34* | (2006.01) |
| *C12Q 1/04* | (2006.01) |
| *C12Q 1/18* | (2006.01) |
| *C12Q 1/686* | (2018.01) |
| *G01N 21/3577* | (2014.01) |
| *G01N 21/359* | (2014.01) |
| *G01N 21/39* | (2006.01) |
| *G01N 21/45* | (2006.01) |
| *G01N 21/64* | (2006.01) |
| *G01N 21/77* | (2006.01) |
| *G01N 21/78* | (2006.01) |
| *G01N 27/414* | (2006.01) |
| *G01N 30/12* | (2006.01) |
| *G01N 30/68* | (2006.01) |
| *G01N 30/70* | (2006.01) |
| *G01N 30/72* | (2006.01) |
| *G01N 30/88* | (2006.01) |
| *G01N 33/00* | (2006.01) |
| *G01N 33/18* | (2006.01) |
| *G01N 33/50* | (2006.01) |
| *G01N 33/53* | (2006.01) |
| *G01N 33/543* | (2006.01) |
| *G01N 33/68* | (2006.01) |
| *G01N 33/74* | (2006.01) |
| *G01N 35/00* | (2006.01) |
| *G01N 35/10* | (2006.01) |
| *G06T 7/00* | (2017.01) |
| *G06T 7/90* | (2017.01) |
| *H10K 10/46* | (2023.01) |
| *H10K 85/00* | (2023.01) |
| *H10K 85/20* | (2023.01) |

(52) U.S. Cl.
CPC ......... *A61B 5/1477* (2013.01); *A61B 5/6803* (2013.01); *A61L 2/03* (2013.01); *A61L 2/10* (2013.01); *A61L 2/26* (2013.01); *A61M 15/02* (2013.01); *A61M 16/105* (2013.01); *A62B 18/02* (2013.01); *A62B 23/02* (2013.01); *A62B 23/025* (2013.01); *B01D 39/1623* (2013.01); *A41D 13/11* (2013.01); *A61M 2205/3303* (2013.01); *B01D 2239/0414* (2013.01)

(58) Field of Classification Search
CPC .... B01D 2239/0258; B01D 2239/0622; A61L 2209/14; A61L 2/03; A61L 2/10; A61L 2/26; A61L 9/16; A61L 2209/111; G01N 33/0004; A41D 13/1192; A41D 13/11; A61B 5/082; A61B 5/1468; A61B 5/1477; A61B 5/6803
See application file for complete search history.

(56) References Cited

U.S. PATENT DOCUMENTS

| | | |
|---|---|---|
| 8,366,625 B2 | 2/2013 | Burns et al. |
| 9,562,855 B1 | 2/2017 | Yoon et al. |
| 9,678,005 B1 | 6/2017 | Yoon |
| 2004/0250683 A1* | 12/2004 | Soane ............... B01D 46/10 55/528 |
| 2007/0163588 A1* | 7/2007 | Hebrank ........... A61M 16/0069 128/205.29 |
| 2012/0016252 A1* | 1/2012 | Melker ................ A61B 5/4821 600/532 |
| 2016/0317848 A1* | 11/2016 | Zilberstein ................ B03C 3/70 |
| 2016/0361674 A1* | 12/2016 | Swaminathan ........ B01D 39/04 |
| 2018/0144092 A1* | 5/2018 | Flitsch ..................... A61B 5/68 |
| 2021/0386133 A1 | 12/2021 | Doyle |
| 2021/0387143 A1 | 12/2021 | Doyle |
| 2023/0103369 A1* | 4/2023 | Gluckman ....... G01N 33/56983 435/5 |

OTHER PUBLICATIONS

"Panda" http://www.panda-pcb.com/html/Products/Interdigital-Electrodes.html (Year: 2019).

\* cited by examiner

SYSTEM FOR MOLECULAR IMPRINTED PROTECTIVE FACE MASK

FIELD OF THE INVENTION

This invention relates to a protective face mask and more particularly relates to a molecular imprinted anti-microbial protective face mask.

BACKGROUND

Protective face masks of various designs have traditionally been used in medical and industrial settings to shield the face and respiratory system of the wearer from infectious agents, particulate matter, and noxious gasses. Various protective face masks have been designed to exclude various materials or particle sizes. For example masks with a designation ending in "95", have a 95 percent efficiency while masks ending in a 99 have a 99 percent efficiency. Masks ending in 100 are 99.97 percent efficient which is the same as a HEPA quality filter. An "N" labeling designates "non-oil;" signifying that the mask is effective in a work environment with no oil particles present. Other masks ratings are R (resistant to oil for 8 hours) and P (oil proof).

Similarly the "0.3" designation indicates that the masks filters out contaminants like dusts, mists and fumes with minimum particulate size of 3 microns.

The filtration material on a mask is typically an electrostatic non-woven polypropylene fiber. Additional technologies may infuse mask surfaces with various metal ions such as copper to provide some degree of antimicrobial function. However, current mask surface coating technologies do not incorporate all desirable aspects, such as agent specific anti-microbial action. Thus, a need exists for a device incorporating the action of a specific molecules and/or a mixture of molecules targeted to specific agents including specific pathogens.

SUMMARY

From the foregoing discussion, it should be apparent that a need exists for protective face mask that would protect against specific infectious agents. It should further be apparent that a need exists for a protective face mask with anti-microbial properties. Beneficially, such an apparatus would be re-usable, and self-cleaning.

The present invention has been developed in response to the present state of the art, and in particular, in response to the problems and needs in the art that have not yet been fully solved by currently available protective face masks. Accordingly, the present invention has been developed to provide a molecular imprinted protective face mask that overcomes many or all of the above-discussed shortcomings in the art.

Provided herein is a system for an interactive biofunctional molecular imprint apparatus, the system comprising a face mask or similar personal protective equipment for cleansing air, and/or detecting hazardous substances and infectious pathogens in the air, a filtering component comprising one or more air-permeable layers of molecular imprinted fabric, woven material, non-woven material and/ or a porous material positioned to contact airborne and/or microdroplet-borne molecules during use, a bioactive molecular imprint wherein an imprinted cavity is of at least one of a bioactive molecule that captures a specific airborne and/or microdroplet-borne molecule and a protein with a binding site that captures a specific airborne and/or microdroplet-borne molecule, an electronic enhancement, a remote connection comprising at least one of an electrical, digital, or other remote connection, a transmitting module, a receiving module, and a power source.

In some embodiments the electronic enhancement comprises at least one of an interdigital electrode, a semiconductor, a nanoparticle quantum dot, a nano-island, a quantum wire, other nanostructured component, a sensor wire, a piezoelectric element, an acoustic waveguide, an optical waveguide, an optical fiber, an ultrasonic transducer, and a laser. The electronic enhancement sometimes at least one of generates a static and time-varying electrical field, produces an electron wave function configuration that dynamically reconfigures the electron charge distribution within the molecular imprint, enables fine tuning of the imprinted cavity to enhance its response to a range of molecules, generates at least one of ultrasonic and electromagnetic waves providing energy to free molecules from the imprinted cavity, mechanically agitates a biomolecule to induce its interaction with or release from the molecular imprint cavity and re-activates the specific molecule capture function of the imprinted cavity.

In certain embodiments the system comprises at least one of a remote data and communications manager and a database and wherein the remote data and communications manager is at least one of an internet, a cloud system, and other digital technology. At least one of the filtration component and the molecular imprint cavity may comprise a biosensor for at least one of a specific health condition, a specific type of pathogen, a specific type of pollutant, a specific type of allergen, and a specific environment or condition and/or may be customized to a specific user or set of users.

In various embodiments the biosensor comprises a molecular imprinted polymer surface comprising at least one of surface plasmon resonance (SPR), surface-enhanced Raman spectroscopy (SERS), fluorescence quenching of semiconductor quantum dots, photoluminescence, UV-visible spectroscopy, electrochemical sensors (conductivity, capacitance, impedance, potentiometry, and voltammetry measurements), piezoelectric (quartz crystal microbalance, surface acoustic wave (SAW), pulse-echo ultrasound, through-transmission ultrasound, and phased-array ultrasound) sensors, and biomimetic microchips with micropatterned imprinted polymers.

The system may further comprise at least one of an alarm, a tracking module and a triggerable reservoir of inhalable or other appropriate medication and wherein the triggerable reservoir of medication comprises at least one of a loaded molecular imprint cavity and other storage medium. The specific user or set of users sometimes comprises persons with compromised lung function and the biosensor senses restricted air flow through a porous material and triggers an alarm and/or release of a bronchodilator and/or other lung treatment. The detection of at least one of a pathogen, contaminant, and other agent from the environment and/or from the user may trigger at least one of an alarm and a treatment action including appropriate medication to at least one of the mask and the tracking module.

In certain embodiments the biosensor further comprises a detection module to detect a pathogen or other agent and the detection module communicates to at least one of the alarm, the medication repository, the tracking module, the cloud system, the internet, and the database.

In some embodiments the air filtering component comprises an air-permeable material comprising at least one of paper, polymer foam, woven fabric, knitted fabric, non-woven fabric, melt-blown fabric, ion-infused fabric, a non-fabric material and a hydrophilic material to capture microscopic airborne droplets to enable the interaction of the molecular imprint cavities with airborne hazardous substances and/or infectious pathogens in an aqueous environment.

The system sometimes comprises one or a plurality of types of molecular imprint cavities and the one or more layers of the filtering component may catalyze a biochemical reaction with an airborne and/or microdroplet-borne agent to attenuate, neutralize, and/or detect the agent. In various embodiments each layer of the filtering component catalyzes a particular step of a biochemical reaction with an airborne and/or microdroplet-borne agent to attenuate, neutralize, and/or detect the agent.

In certain embodiments layer (n) catalyzes a particular biochemical reaction (p) in a multistep reaction with an airborne and/or microdroplet-borne agent. Layer (n+1) may catalyze a successive biochemical reaction (p+1) in a multistep reaction with an airborne and/or microdroplet-borne agent. The plurality of molecular imprint cavity types may catalyze a multistep biochemical reaction to attenuate, neutralize, or detect an airborne and/or microdroplet-borne agent. The plurality of molecular imprint cavity types sometimes simultaneously catalyze one or more biochemical reactions to at least one of attenuate, neutralize, and detect one or more hazardous airborne and/or microdroplet-borne agents.

In various embodiments the electronic enhancement at least one of reads the binding state of the molecular imprinted cavities to detect hazardous airborne and/or microdroplet-borne agents and triggers re-tuning the imprinted cavities in response to at least one of a completed reaction and a changing molecular environment. A conductive electrode sometimes functions as an interdigital electrode for at least one of enhancing, modulating, and reading the binding state of the imprinted cavities. The interdigital electrode may comprise at least one of comb-shaped interlocking arrays of straight parallel electrodes, a fan-shaped array of radially-oriented electrodes, an array of concentrically-oriented circular electrodes, and arrays consisting of electrodes arranged in more complex geometries such as elliptical, parabolic, hyperbolic, and straight-line angles.

Herein provided is a system for a molecular imprint apparatus, the apparatus comprising a face mask or similar personal protective equipment for cleansing air, and/or detecting hazardous substances and infectious pathogens in the air. In various embodiments the apparatus comprises an air filtering component comprising one or more air-permeable layers of molecular imprinted fabric, woven material, non-woven material and/or a porous material positioned to contact airborne and/or microdroplet-borne molecules during use and comprises a bioactive molecular imprint wherein an imprinted cavity is of a bioactive molecule that captures a specific airborne and/or microdroplet-borne molecule and/or of a protein with a binding site that captures a specific airborne and/or microdroplet-borne molecule. The molecular imprints on the surface of the threads of the fabric and/or the interior pores of the porous material may attenuate, neutralize, and/or detect toxic gases, toxic fumes, hazardous aerosols, or infectious pathogens.

In certain embodiments the air filtering component comprises an air-permeable material comprising paper, polymer foam, woven fabric, knitted fabric, non-woven fabric, melt-blown fabric, ion-infused fabric, a non-fabric material and/or a hydrophilic material to capture microscopic airborne droplets to enable the interaction of the molecular imprints with airborne hazardous substances and/or infectious pathogens in an aqueous environment. The one or more layers of the filtering component may catalyze a biochemical reaction with an airborne and/or microdroplet-borne agent to attenuate, neutralize, and/or detect the agent.

The apparatus sometimes comprises an electronic enhancement comprising at least one of an interdigital electrode, a semiconductor, a nanoparticle quantum dot, a nano-island, a quantum wire, other nanostructured component, a piezoelectric element, an acoustic waveguide, an optical fiber, an ultrasonic transducer, and a laser. In various embodiments the electronic enhancement at least one of generates a static and/or time-varying electrical field, produces an electron wave function configuration that dynamically reconfigures the electron charge distribution within the molecular imprint, enables tuning of the imprinted cavity, generates at least one of ultrasonic and electromagnetic waves, and mechanically agitates a biomolecule to induce its interaction with or release from the molecular imprint cavity.

Layer (n) of the apparatus sometimes catalyzes a particular biochemical reaction (p) in a multistep reaction with an airborne and/or microdroplet-borne agent. Layer (n+1) may catalyze a successive biochemical reaction (p+1) in a multistep reaction with an airborne and/or microdroplet-borne agent. In some embodiments each layer of the filtering component catalyzes a particular step of a biochemical reaction with an airborne and/or microdroplet-borne agent to attenuate, neutralize, and/or detect the agent. The filtering component may comprise one or more layers of porous material comprising fibers of at least one of a plurality of molecular imprint types, conductive electrodes, sensor wires, optical waveguides, and acoustic waveguides.

In various embodiments the plurality of molecular imprint types catalyze a multistep biochemical reaction to attenuate, neutralize, or detect an airborne and/or microdroplet-borne agent. The plurality of molecular imprint types may simultaneously catalyze one or more biochemical reactions to at least one of attenuate, neutralize, and detect one or more hazardous airborne and/or microdroplet-borne agents.

The sensor wires may read the binding state of molecular imprint cavities to detect hazardous airborne and/or microdroplet-borne agents. The air filtering component sometimes comprises a transducer comprising an interdigital electrode and/or other device for at least one of fine-tuning the molecular imprint to enhance its response to a range of molecules, provide electrical energy to free molecules from the imprinted binding site, re-activate the specific molecule capture function of the imprint site, and interact with the molecular imprint to function as a biosensor.

The apparatus biosensor may comprise a molecular imprinted polymer surface comprising at least one of surface plasmon resonance (SPR), surface-enhanced Raman spectroscopy (SERS), fluorescence quenching of semiconductor quantum dots, photoluminescence, UV-visible spectroscopy, electrochemical sensors (conductivity, capacitance, impedance, potentiometry, and voltammetry measurements), piezoelectric (quartz crystal microbalance, surface acoustic wave (SAW), pulse-echo ultrasound, through-transmission ultrasound, and phased-array ultrasound) sensors, and biomimetic microchips with micropatterned imprinted polymers. In some embodiments the conductive electrode functions as an interdigital electrode for enhancing, modulating and/or reading the binding state of the imprinted cavity.

The interdigital electrode sometimes comprises at least one of comb-shaped interlocking arrays of straight parallel electrodes, a fan-shaped array of radially-oriented electrodes, an array of concentrically-oriented circular electrodes, and arrays consisting of electrodes arranged in more complex geometries such as elliptical, parabolic, hyperbolic, and straight-line angles.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Introduction

Molecular imprinting is an advancing technique in the medical device field because of its ability to mimic biologically active binding sites. Molecular imprinting uses artificial binding sites of proteins, sugars, and other biological compounds in order to capture molecules. Numerous two-dimensional and three-dimensional techniques are known in the art for imprinting of surface proteins. Techniques using silica have shown successful specificity for imprinting complex shapes such as hemoglobin. Biomedical applications have utilized molecular imprinting for ex vivo diagnostic methods such as immunoassays (antibody detection), analytical separations, and biosensors for detecting changes in blood sugar. Molecular imprinting is also used in the development of other biosensors and for diagnostic detection of viruses by interacting with antibodies.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to convey a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
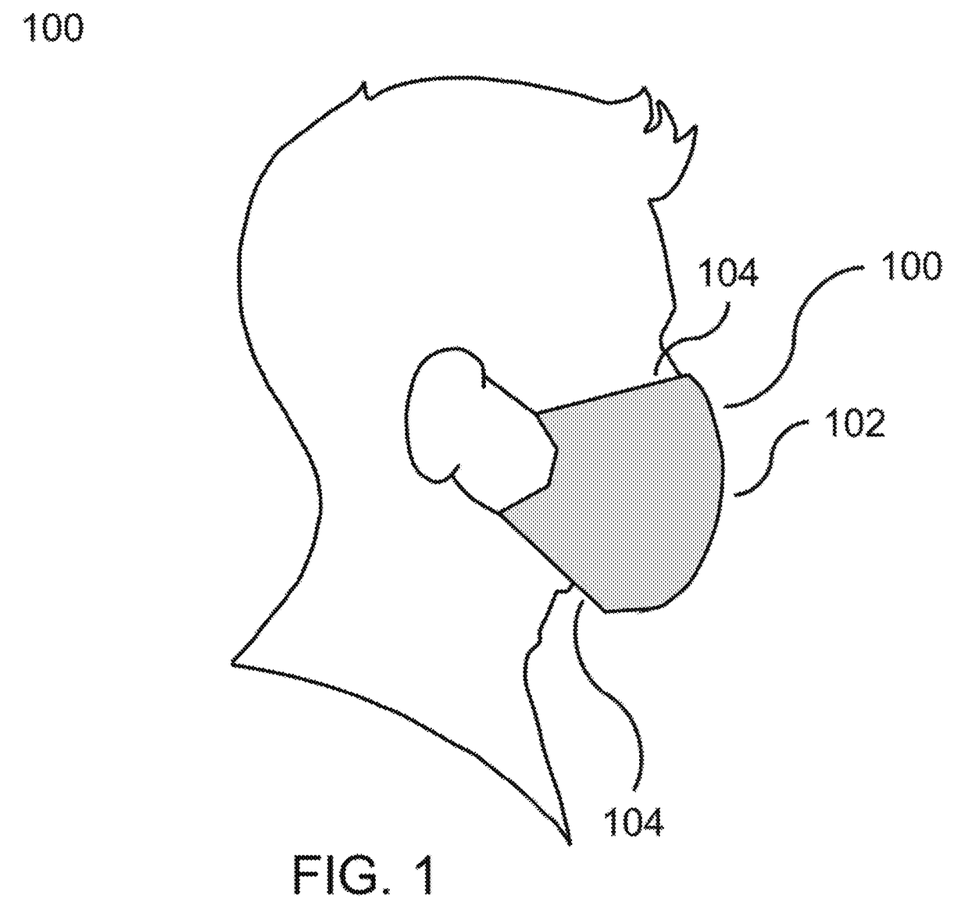
FIG. 1 is a schematic line drawing depicting an embodiment of a molecular imprinted face mask as worn by an individual, comprising a filtering component and a component that holds the filtering component securely against the front of the face over the nose and mouth.

FIG. 1 depicts an embodiment of a molecular imprinted face mask 100 as worn by an individual, comprising an outer surface 102 that holds a filtering component 104 securely against the front of the face over the nose and mouth and a user. The outer surface may comprise an air-permeable material including without limitation paper, woven fabric, knitted fabric, non-woven fabric, melt-blown fabric, ion-infused fabric, polymer foam, or other appropriate material as known in the art.

In various embodiments the filtering component 104 comprises a fabric and/or porous material for air to pass through. The surface of the threads of the fabric and/or the interior pores of the porous material may be coated with molecular imprints that capture, attenuate, neutralize, and/or detect toxic gases, toxic fumes, hazardous aerosols, or infectious pathogens. In certain embodiments a single layer of a molecular imprinted fabric, woven, or non-woven material is used as the filtering component. The fabric or other woven or non-woven material sometimes comprises more than one type of fiber or other material and/or more than one type of molecular imprint. Different types of molecular imprints sometimes attenuate and/or neutralize more than one airborne agent. Different types of molecular imprints sometimes generate a multi-step process in the woven matrix to attenuate and/or neutralize an airborne agent.

Figure 2:
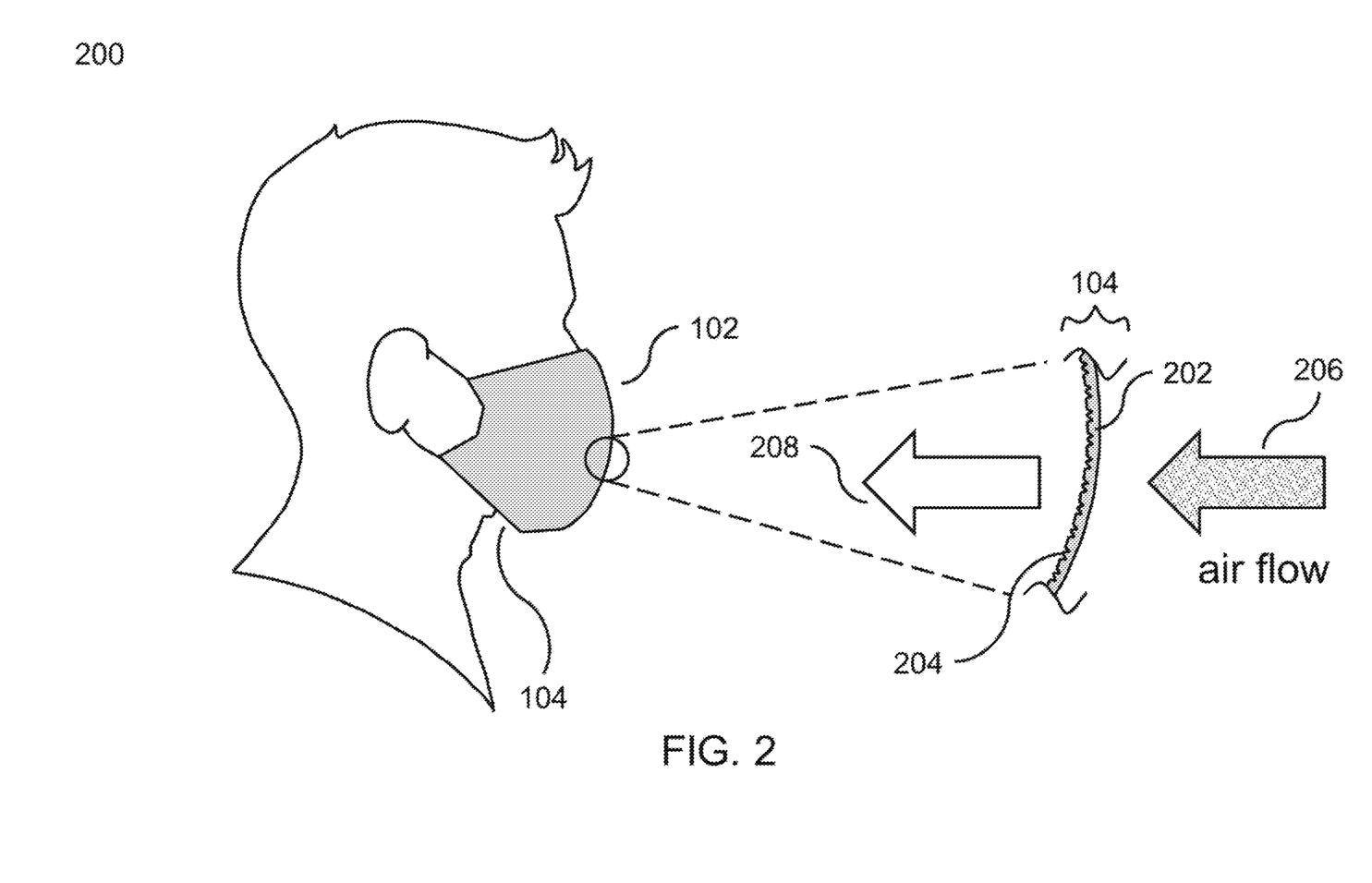
FIG. 2 is a schematic line drawing and expanded section view depicting an embodiment of a molecular imprinted face mask consisting of a single-layered filtering component, composed of a molecular imprinted fabric or other porous material.

FIG. 2 depicts an expanded view of an embodiment of a molecular imprinted face mask 100 comprising a single-layered filtering component 104, an outer surface 102, a thin polymer film 202, and molecular imprints 204 on surface of the polymer film 202. Environmental air 206 passes through the filtering component 104 and filtered air 208 emerges.

In some embodiments the outer surface 102 is coated with the thin polymer film 202. The filtering component 104 may comprise a molecular imprinted fabric or other porous material. The polymer film 202 may be a molecular imprinted polymer with imprinted sites 204 that in various embodiments may capture, sense, destroy, and/or release bacteria, viruses, medications, and various airborne particles.

A molecular imprinted polymer 202 may be created by mixing monomers of the polymer with the molecule (known as the template) to be imprinted. First, the monomers cluster and conform around the template. Second, the monomers polymerize with the template in place. Third, the template is removed from the polymer, thus leaving a mold or imprint 204 of the molecule in a polymer matrix. The monomers can be polymerized into nanoparticles or thin films. To create the molecular imprinted face mask 100 described herein, the monomers may be polymerized as a thin film 202 on the porous surface 102 of the face mask 100 or on the surfaces of fibers comprising a fabric or woven filtering component. Alternative, the monomers may be polymerized directly as fibers and incorporated into a fabric or woven filtering component.

Various methods for the fabrication of molecular imprinted polymers as thin films on a solid substrate are known in the art, and include spin coating, polymer brushes, dip coating using a silicon substrate, self-assembling monolayers, drop coating, spray coating, grafting, electropolymerization, and sol-gel processes. Micropatterned thin films of molecular imprinted polymers can also be manufactured using various lithography methods such as UV-mask lithography, soft lithography, micro-stereo lithography, and nano-imprint lithography.

The molecular imprinted face mask 100 may be fabricated in a variety of different models comprising different sets of molecular imprints 204. A model could then be available for capturing various types of pathogens including bacteria and viruses such as the COVID-19 virus. In certain embodiments pathogens trapped by the molecular imprints 204 may also be inactivated or killed. Mechanisms may include, without limitation, chemical, biological, electrical, sonic, and UV light, applications as described above.

Figure 3:
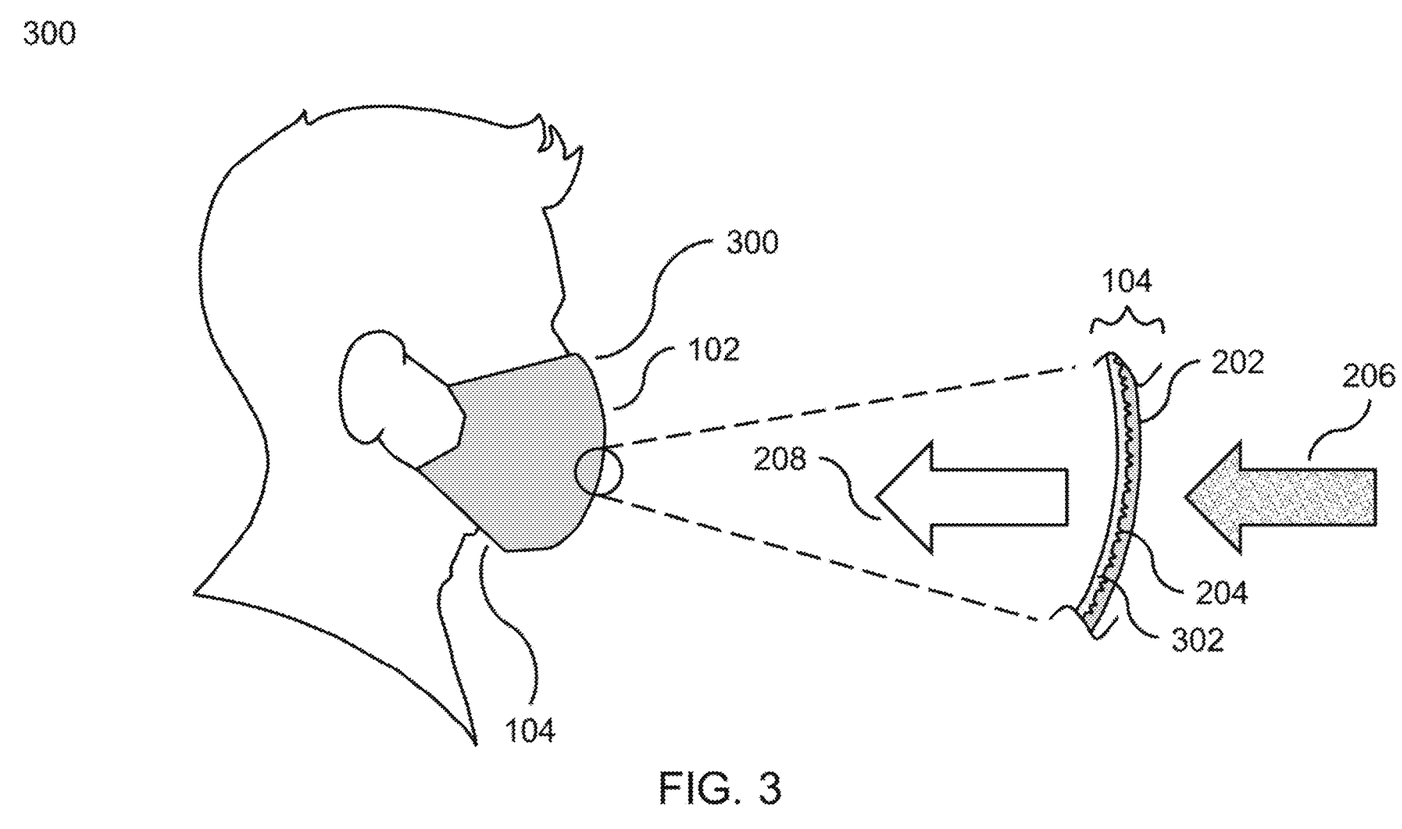
FIG. 3 is a schematic line drawing and expanded section view depicting an embodiment of a molecular imprinted face mask consisting of a double-layered filtering component, composed of fabric or other porous material layers with molecular imprints, different types of molecular imprints, conductive electrodes, microsensors, sensor wires, optical waveguides, and/or acoustic waveguides.

FIG. 3 depicts an embodiment of a multi-layer molecular imprinted face mask 300 in accordance with the present invention. As depicted, the multi-layer molecular face mask 300 comprises an outer surface 102, a filtering component 104, a thin polymer film 202, molecular imprints 204 on surface of polymer film 202, and an additional filtering layer 302. In various embodiments of the invention, two or more layers of a molecular imprinted fabric or other material are used to generate a multi-step process to attenuate, neutralize, and/or detect toxic, hazardous, or infectious agents in the air. Two or more layers of a molecular imprinted fabric may be used to detect toxic, hazardous, or infectious airborne agents in one layer, and to attenuate and/or neutralize these agents in the other layer.

Figure 5:
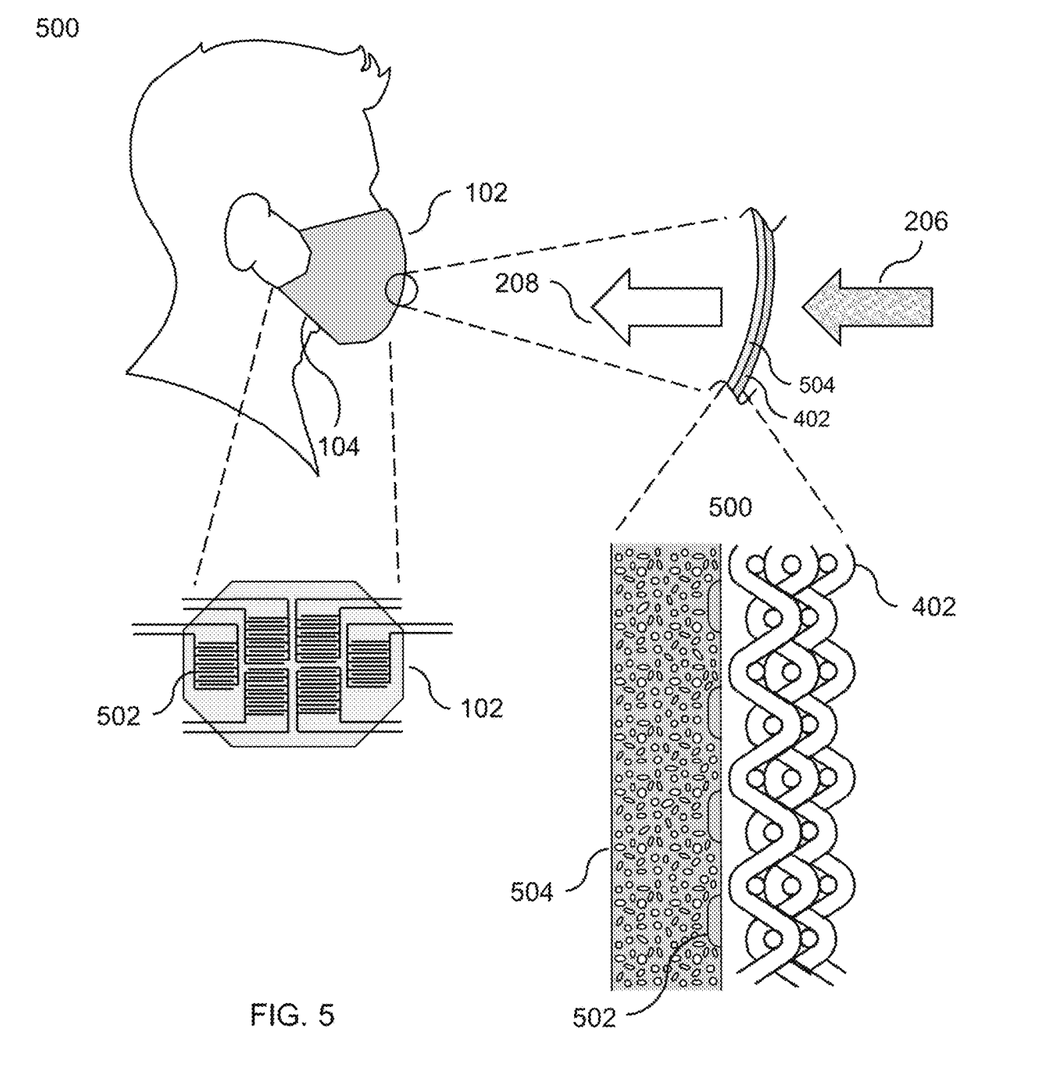
FIG. 5 is a schematic line and surface drawing depicting an expanded view of an embodiment of an electronically enhanced molecular imprinted face mask in accordance with the present invention.

The strategically placed imprints 204 as shown on the molecular imprinted face mask 300 may be those of an antigen or binding site for a bacteria or virus such as COVID-19. Imprinting of an antigen or binding site may be accomplished through template imprinting techniques. Antigen or binding site molecules are obtained as a template by absorption onto a silicate mineral along with a buffer. The sample is heated and left to cool. Afterwards the sample is rinsed with deionized water to remove the buffer. The remaining sample may be coated with a disaccharide. A plasma deposition (hexafluoropropylene) may be deposited onto the sample where it will be placed in a plasma reactor to remove the template protein. Finally, a solvent may wash away any remains of the template protein.

In certain embodiments the thin polymer film 202 covers majority of mask 300 area for biochemically interacting with airborne particles. A pattern of molecular imprints 204 of different molecular species on a polymer film 202 may be used as described above. Molecular imprints may function as "phantom" or "virtual" molecules or binding sites to capture and immobilize pathogen molecules, to sense and report them, to kill or inactive them, and to release them during cleaning.

FIG. 4 depicts an embodiment of a woven filtering component 400, composed of fibers with molecular imprints 402, different types of molecular imprints 404, positively charged conductive electrodes 406, negatively charged conductive electrodes 408, sensor wires, optical waveguides, and/or acoustic waveguides 410. In some embodiments an electronically generated physical mechanism may release proteins from trapped on the surface of the polymer film 202. Ultrasonic waves may be generated in the mask 100, 300 or an external device 702 and transmitted to the mask surface 102 and polymer film 202 via waveguide principles. An acoustic waveguide 410 may comprise metal incorporated into the filtering component 104. Such waveguide principles are identical to those used to propagate light along an optical fiber. In this manner the protective face mask 100 may be safely cleaned between uses and pre-loaded molecular imprints may be emptied of medication and/or other cargo.

In certain embodiments conductive wires function as interdigital electrodes 406 and 408 that enhance, modulate and/or read the binding state of the imprints 204. Optical and/or acoustic waveguides 410 may function as sensor components in conjunction with the molecular imprints 204. Optical and/or acoustic waveguides 410 in a fabric, woven, or non-woven material may function to attenuate or neutralize a hazardous airborne agent. For example, ultraviolet (UV) light transmitted by optical waveguides 410 may attenuate or neutralize a virus captured by molecular imprints 202 on the optical waveguides 410, and/or other fiber components in the fabric, woven or non-woven matrix.

FIG. 5 depicts an expanded view of embodiment of an enhanced molecular imprinted filtering component 500 in accordance with the present invention. As depicted the electronically enhanced molecular imprinted filtering component 500 comprises a polymer coating 202, molecular imprints 204, and interdigital electrodes 502 embedded within the filtering component 104, embedded within an air-permeable polymer support substrate such as polyurethane foam 504, and/or positioned on the surface of the mask 102 as biosensors. Molecular imprints 204 may be loaded with material 506 comprising medications or other substances.

Biosensing molecular imprinted polymer surface technologies include surface plasmon resonance (SPR) techniques, surface-enhanced Raman spectroscopy (SERS), fluorescence quenching of semiconductor quantum dots, photoluminescence, UV-visible spectroscopy, electrochemical sensors (conductivity, capacitance, impedance, potentiometry, and voltammetry measurements), piezoelectric (quartz crystal microbalance, surface acoustic wave (SAW), pulse-echo ultrasound, through-transmission ultrasound, and phased-array ultrasound sensors, and biomimetic microchips with micropatterned imprinted polymers. The molecular imprint biofunctional devices provided herein may combine biosensors with bioactive molecular imprints and apply them to a protective face mask.

In certain embodiments the electronically enhanced molecular imprinted filtering component 500 detects molecules in contact with the molecular imprints 204. The electronically enhanced molecular imprinted filtering component 500 sometimes detects specific pathogen molecules, providing information on probable exposure and the relevant venue. In various embodiments the electronically enhanced molecular imprinted filtering component 500 detects particles, pollutants, and gasses, and may alert the wearer to the status of the breathing environment in real time.

In some embodiments the molecular imprinted protective face mask is configured for a specific type of pathogen, a specific type of pollutant, a specific type of allergen, a specific environment or condition and/or is customized to a specific user or set of users. The electronically enhanced molecular imprinted filtering component sometimes comprises a triggerable reservoir of airborne medication 504 which may comprise a loaded molecular imprints 202 and/or other storage medium. The specific user or set of users sometimes comprises persons with compromised lung function. The biosensor may sense restricted air flow through the mask and trigger release of a bronchodilator and/or other lung treatment. In certain embodiments the biosensor is tuned to sense specific volatile organic compounds (VOCs) in the exhaled breath of the user and to trigger an alert and/or release of an appropriate medication. Non-limiting examples of using the molecular imprinted face mask to sense VOCs in exhaled breath to diagnose, monitor, and/or treat medical conditions include asthma, hyperglycemia in diabetic patients, disease progression in patients with renal failure, and cancer.

Figure 6:
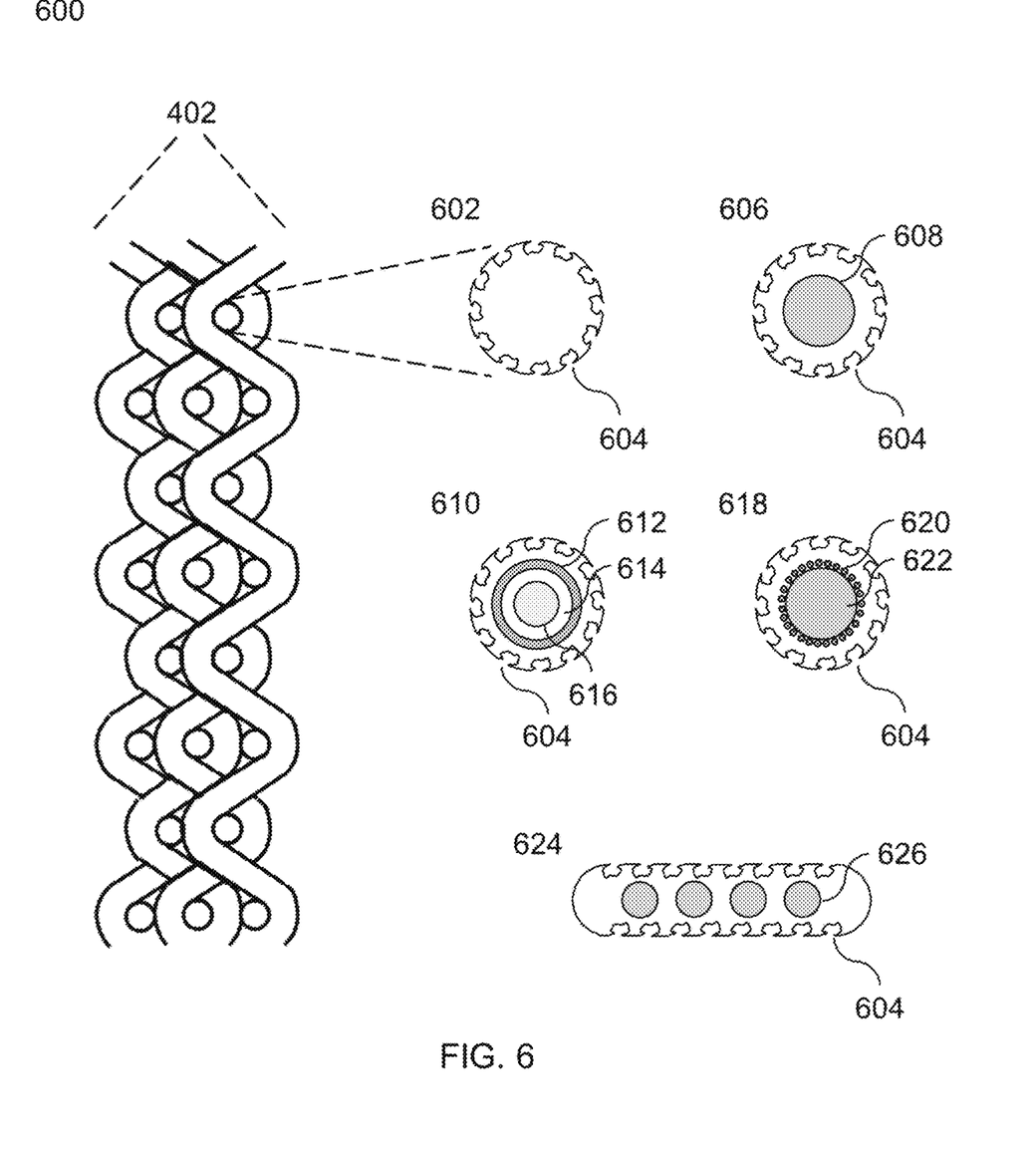
FIG. 6 is a schematic line and surface drawing depicting an expanded section view of an embodiment of an electronically embedded molecular imprint protective face mask in accordance with the present invention, showing semiconductor and nanoparticle quantum dots embedded within a mask element in accordance with the present invention.

FIG. 6 depicts an expanded section view of an embodiment of an electronically enhanced molecular imprinted face mask 500 in accordance with the present invention. As depicted, the electronically enhanced molecular imprinted face mask is comprised of a fabric or woven filtering component 402 with simply structured molecular imprinted fibers 602, with molecular imprints on the surface of the fiber 604 and electronically enhanced with interdigital electrodes 502. Alternatively, complexly structured molecular imprinted fibers may be used with surface molecular imprints 604 combined with internal electrical components 602, 606, 610, 618, and 624. These complexly structured fibers include those with a conductive electrode core 608, a coaxial conductive core 612 and conductive shield 616, a conductive electrode core 622 surrounded by quantum dots 620, and/or multiple conductive cores 626. As depicted, fibers with multiple conductive cores may be configured as a ribbon 624, increasing the surface area of the fiber and thereby the density of molecular imprints 604.

In one embodiment the electronically enhanced molecular imprinted face mask 500 comprises a polymer film 202, molecular imprints 604, an embedded semiconductor or piezoelectric polymer 614, embedded quantum wires 626, or nanoparticle quantum dots 620. In some embodiments, quantum dots 620 underneath the molecular imprints 604 are used to configure the imprints 604. In certain embodiments the quantum dots 620 or wires 626 are custom-engineered to produce unique electron wave function configurations that modulate the response of the molecular imprints 604. The quantum dots 620, or wires 626 may be used to dynamically reconfigure the electron charge distribution within the molecular imprints 604, thereby creating a tunable molecular imprint 604 at the quantum level. Such charge distribution may influence processes such as the capture, sensing, reporting, deactivation, or destruction of pathogens or other molecules.

For non-limiting example, static electric fields (also known as direct-current or DC fields) have been shown to repel, attract, or capture airborne molecules, particles, or gases. Such static electric fields are sometimes generated on the surface of the electronically enhanced molecular imprinted face mask 500, with the use of interdigital electrodes 502 deposited onto or into the surface of an insulating material (e.g. polyurethane foam), but lying beneath the polymer film 202 or molecular imprinted fabric 402, and corresponding molecular imprints 604.

In various embodiments electric fields, ultrasonic waves, electromagnetic waves, or quantum dots provide additional energy to free molecules from the imprint binding sites. This may function in the fabrication of the molecular imprints and in re-activation of the binding function of imprint sites that have been de-activated by the bonding of free molecules to the imprints.

In certain embodiments high frequency ultrasonic waves (10 MHz-10 GHz) or light (infrared to ultraviolet) may impact pathogens or other materials bound to the molecular imprints 204. The ultrasonic or light waves may be generated in the electronically enhanced molecular imprinted face mask 500 or in an attachment and conducted to the face mask 500 via waveguide principles, including without limitation an acoustic waveguide or optical fibers embedded into the face mask 500. The electronically enhanced molecular imprinted face mask 500 sometimes comprises a semiconductor. In certain embodiments the semiconductor comprises silicon into which ultrasonic transducers or lasers are fabricated on microchips and embedded into the filtering component 104 to locally excite the molecular imprints.

In certain embodiments high-frequency ultrasonic waves (10 MHz-10 GHz) are generated locally in the electronically enhanced molecular imprinted face mask 500 by embedded piezoelectric elements and conductive electrodes 612, 614, and 616. In some embodiments an ultrasonic wave is generated on the electronically enhanced molecular face mask component 500 that mechanically agitates bound protein molecules or other materials and induces their separation from the imprints 204. Piezoelectric elements may include but are not limited to fibers and thin films.

Figure 7:
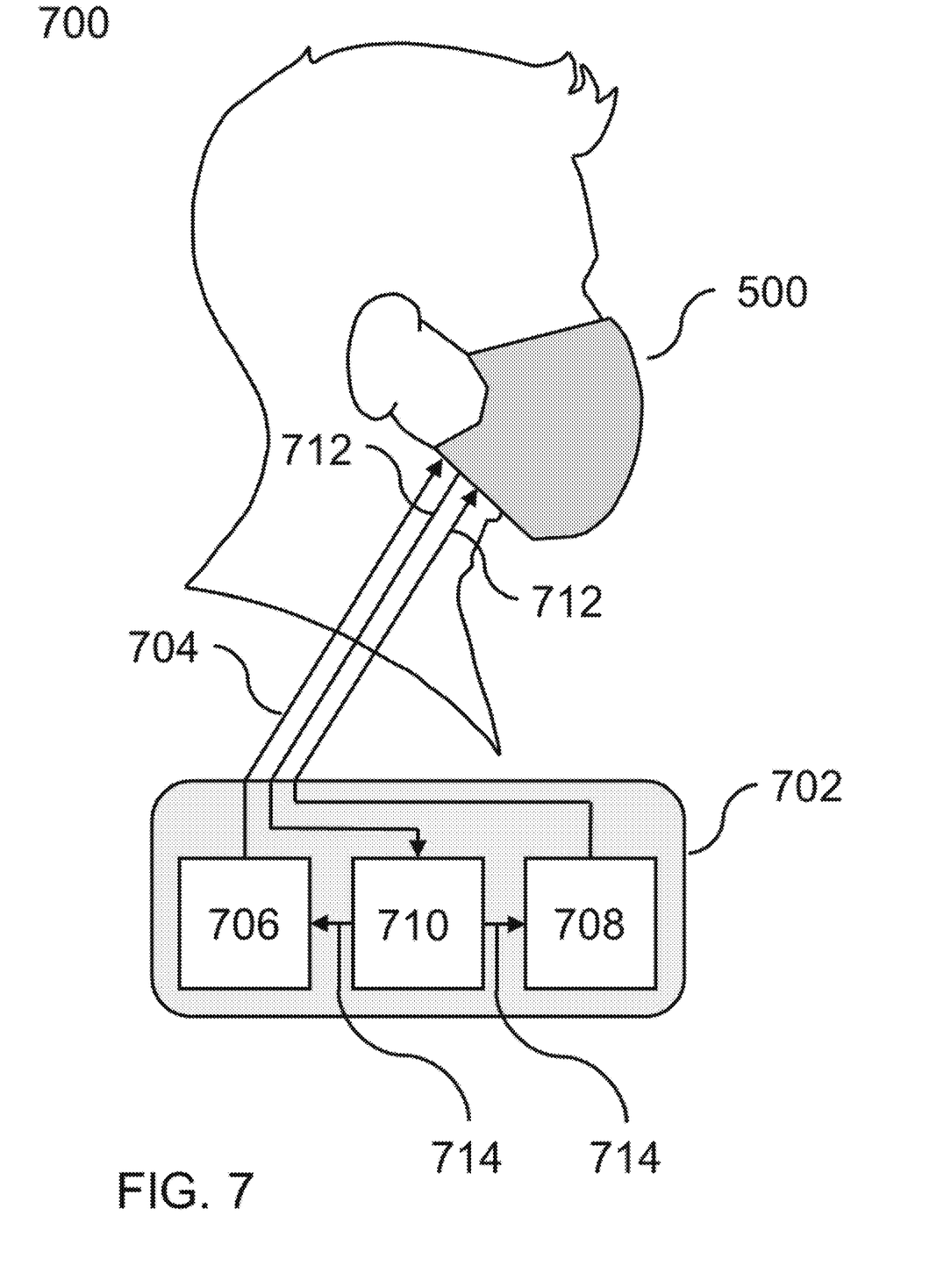
FIG. 7 is a schematic line and surface drawing depicting an embodiment of a system for an electronically enhanced molecular imprint protective face mask in accordance with the present invention.

FIG. 7 depicts an embodiment of a system for an electronically enhanced molecular imprinted protective face mask in accordance with the present invention, the system comprising an electronically enhanced molecular imprinted protective face mask 500, an attachment 702, a supply tube 704, a medication repository 706, a power supply component 708, and a detection component 710. The attachment 702 may be connected to the face mask 500 either physically or remotely. In certain embodiments electric current, light waves, sound waves or other energy is generated in the attachment 702 by a power supply component and conducted to the face mask 500 via wires, tape, channels, optical waveguides, or other conduit 712. In some embodiments the attachment 702 is a triggering device that communicates with the mask 500 to generate an energetic response within the mask 500. In various embodiments the attachment 702 comprises a triggerable repository for inhalable or other appropriate medication 706. Medication may be supplied to the mask 500 via a tube 704 or other channel. The medication repository 706 may be located on the attachment 702 or in any convenient location on the face mask 500.

In some embodiments, the attachment 702 contains a detection component 710 to electronically process sensor signals received from the mask 500 via wires, tape, channels, optical waveguides, wireless radio-frequency communication, or other conduit 712. In some embodiments, the detection component 710 also provides a readable output to the mask wearer on the level and/or type of hazardous substance or infectious pathogen detected by the face mask 500. In certain embodiments, the detection component 710 generates a triggering signal based on sensor input from the mask 500. The triggering signal is communicated via electrical wires 714 to the medication repository 706, where it triggers the release of medication. In certain embodiments, the triggering signal from the detection component 710 is communicated via electrical wires 714 to the power supply component 708, where it triggers at least one of fine-tuning the molecular imprint to enhance its response to a range of molecules, providing electrical energy to free molecules from the imprinted binding site, re-activating the specific molecule capture function of the imprint site, and interacting with the molecular imprint to function as a biosensor.

The detection component may contain at least one of a photodetector to convert optical signals from optical fibers to electrical signals, an ultrasound transducer to convert acoustic signals from acoustic waveguides to electrical signals, a spectrometer to analyze optical signals with molecular spectroscopy (for example surface plasmon resonance, surface-enhanced Raman, quantum dot fluorescence quenching, photoluminescence, and UV-VIS-IR spectroscopy), a multiplexer for a plurality of sensor channels, an amplifier to amplify sensor signals, a rectifier for radio-frequency signals such as ultrasonic signals, an electronic filter and/or discriminator to separate signals from noise, and a trigger signal generator.

Figure 8:
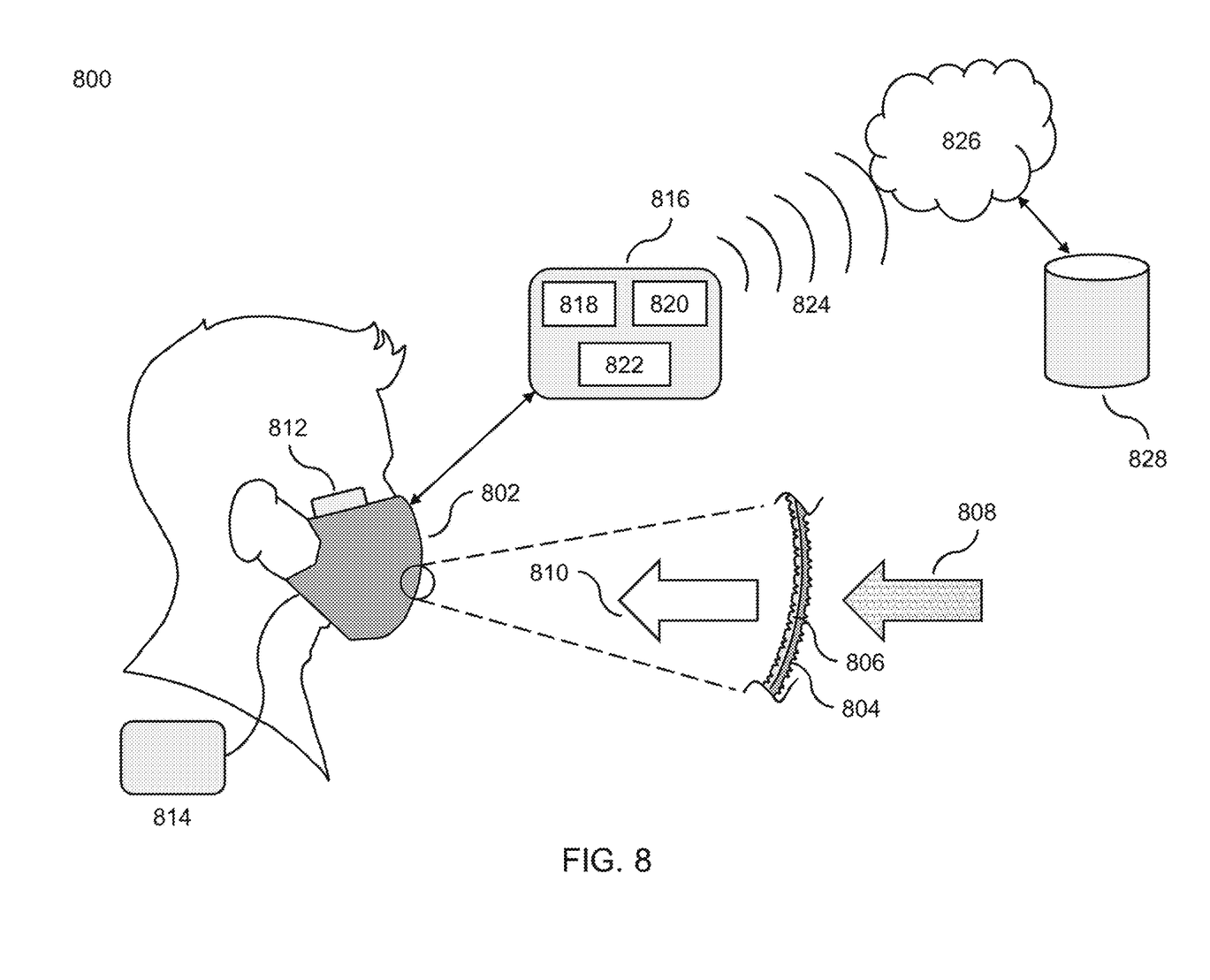
FIG. 8 is a schematic line and surface drawing depicting and embodiment of a system for a molecular imprinted protective face mask.

FIG. 8 depicts an embodiment of a system for a molecular imprinted protective face mask, comprising a face mask 802, one or more layers of molecular imprints 804, an electronic enhancement 806, outside air 808, filtered or treated air 810, a medication repository 812, a power source and detection module 814, communication module 816, a receiving module 818, a transmitting module 820, a tracking module 822, a remote connection 824, a remote data and communications manager 826, and a database 828.

Communication between the electronic enhancement of the mask 806 and a database 828 provides the ability of the molecular imprinted face mask to selectively adapt to changing environmental hazards, specifically to detect, analyze, and counter a plurality of airborne threats. An example of the mask's adaptive ability is the following:

First, the environment is analyzed for a range of hazardous agents and pathogens by sending a sequence of control signals from the database 828 to the mask 802 via a communications manager 826, a remote connection 824, and a receiving module 818. Examples of a remote connection 824 include but are not limited to ethernet, wireless, and/or optical fiber connections The control signals electronically tune the wave functions of the molecular imprints 804 through the electronic enhancement 806, and they sweep the sensitivity range of the imprints across different molecular or pathogen species. The electronic enhancement 806 is then used in combination with the molecular imprints 804 to sense the presence and concentration of hazardous molecules and/or pathogens. The sensor data is processed by the detection component 814. The processed sensor data is transmitted back to the database by means of a transmitting module 820, remote connection 824, and communications manager 826.

Second, the mask is tuned to selectively capture, attenuate, and/or neutralize the principal hazardous molecule or pathogen in the environment. A control signal is sent from the database 828 to the mask 802 via a communications manager 826, a remote connection 824, and a receiving module 818. The control signal electronically tunes the wave functions of the molecular imprints 804 through the electronic enhancement 806 to selectively interact with the principal hazardous molecule or pathogen.

Another function of the sensing and communication capabilities of the molecular imprinted protective face mask system is to use the sensor data from one or more masks to map the spatial extent and time-dependent changes of a hazardous molecule or pathogen in the environment. This data would be particularly valuable to the epidemiological monitoring of a disease such as COVID-19, for example to identify disease hotspots (geographically localized increases of infection), and spikes or surges in the infection rate (acceleration of infection rates).

EXAMPLES

Example 1: The Manufacture of a Molecular Imprinted Face Mask

A procedure for creating molecular imprints on face mask comprises the following steps. (1) Molecules of a specific airborne molecule (for example, COVID-19 virus) or a specific protein that functions as an antigen, antibody, or binding site for the airborne molecule are absorbed onto the surface of a thin mica sheet. (2) A buffer is added to neutralize the pH of the mica-protein surface. (3) The mica sheet-buffer solution is heated and subsequently cooled. (4) The mica sheet is rinsed with deionized water and spin cast with a disaccharide to allow coating.

The hydroxyl groups on the disaccharide molecules, combined with the surface polar residues of the protein molecules, facilitate the formation of hydrogen bonds during dehydration. Hydrogen bonds are vital for molecular recognition in biological signaling. The disaccharide coating also protects the protein molecules from dehydration and damage during the following plasma deposition process, thus preserving the fidelity of the imprinted cavities.

(5) A thin fluoropolymer film is deposited onto the mica surface using radio-frequency glow-discharge plasma deposition and hexafluoropropylene. (6) The fluoropolymer film is removably attached to a temporary support surface. The surface provides mechanical support for the fluoropolymer film. (7) The mica sheet is peeled from the supported fluoropolymer film. (8) The protein molecules are removed from the fluoropolymer film using a solvent wash, leaving behind molecular imprints of the protein. (9) The fluoropolymer film is incorporated into a woven or non-woven air-permeable surface.

For the synthesis of molecular imprinted fibers, silica capillaries are used as molds to replace the mica sheet. As in the procedure above, the target molecules are absorbed onto the interior surface of the capillary. The support polymer is then introduced into the capillary and polymerized. The capillaries are then etched away to free the imprinted polymer fibers. Another approach for the synthesis of molecular imprinted fibers is to use silica fibers as a permanent substrate for the molecularly imprinted polymer. The silica fibers are coated with a thin layer of the molecularly imprinted polymer and the polymer is then polymerized.

The above procedures may be utilized to molecularly imprint a set of diverse proteins onto a face mask in a specific spatial pattern. Non-limiting examples of proteins and other macromolecules that could be used for each molecular-imprinted polymer region on the face mask include the following: (1) angiotensin-converting enzyme 2 (ACE-2), which functions as the entry point into cells for the COVID-19 virus and other coronaviruses; (2) complex sugar chains (glycans) such as sialic acids of various chemical forms, which function as the entry point into cells for influenza viruses; and (3) receptor molecules in the immunoglobulin superfamily (IgSF), which function as entry points into cells for the measles virus and rhinovirus (common cold).

In the event that certain molecular imprints do not function similarly to their protein molecule counterparts, molecular "outprints" can be created by a stamping method that first creates the molecular imprints on nanoparticles. A polymer film is then stamped with these molecularly imprinted nanoparticles, creating a negative image of the molecular imprint, or an outprint. These molecular outprints will have the same positive shape as the original molecule, and may, therefore, have a functionality more similar to the original molecule.

Example 2: Detection of Virus Proteins

Protein-based molecular imprints have additionally been explored for the detection of virus proteins and even whole viruses. In some cases, a polymer is cross-linked and co-polymerized in the presence of a target molecule or protein. This target acts as a template for creating a cast. Once the cast is removed, it creates space for an active binding site. Molecular imprinting is supported by extensive research in the last decade, yet the application of imprinting protein-binding sites on dry surfaces for capture, sensing, activation and deactivation of airborne molecules remains to be investigated.

Figure 4:
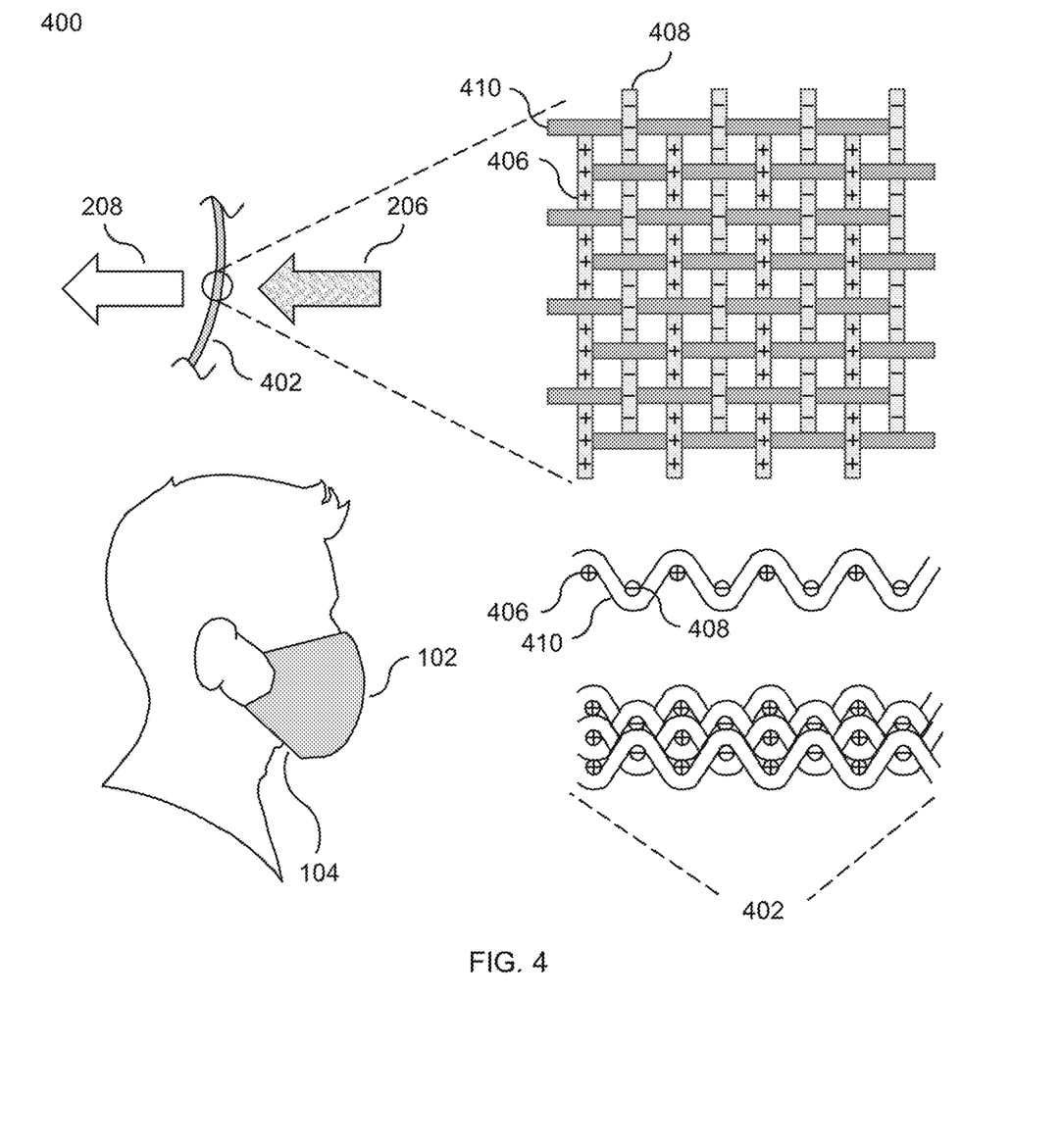
FIG. 4 is a schematic line drawing and expanded section view depicting an embodiment of a molecular imprinted face mask consisting of a woven filtering component, composed of fibers with molecular imprints, different types of molecular imprints, conductive electrodes, sensor wires, optical waveguides, and/or acoustic waveguides.

Previous studies have demonstrated the binding of influenza viruses to molecular imprints using aqueous solutions of viruses in contact with an imprinted polymer. In the event that an aqueous environment may be necessary for the binding of viruses to molecular imprints, evidence supports a mechanism for the capture, sensing, activation and deactivation of airborne viruses by a molecular imprinted face mask. This evidence includes the fact that many pathogenic viruses such as influenza and COVID-19 are primarily spread by microscopic airborne droplets (microdroplets) that are dispersed from an infected person by coughing, sneezing, singing, and/or speaking. Upon passing through a molecular imprinted face mask, the microdroplets are trapped by the fibers 402 and/or pores 504 in the mask's filtering component 104, and simultaneously come into contact with molecular imprints 604 on the fiber and/or pore surfaces. Consequently, the viruses are brought into contact with the molecular imprints in the aqueous environment of the microdroplets.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:
1. A filtering apparatus comprising:
   a filtering component comprising one or more air permeable layer comprising:
      imprinted cavities on at least a portion of a filtering material to capture an airborne and/or microdroplet-borne element or elements; and
      at least a portion of an electronic enhancement integrated within at least a portion of at least one layer comprising the filtering material, in which the at least a portion of the electronic enhancement and the at least a portion of at least one layer are configured to form a substantially uniform filtering matrix region for the filtering apparatus.

2. The filtering apparatus of claim 1 wherein an airborne and/or microdroplet-borne element comprises a molecule or compound and the imprinted cavities comprise at least one type of one or more types of imprinted cavities, in which a type of imprinted cavity is configured to capture a specific molecule or compound using a binding site or sites.

3. The filtering apparatus of claim 1 further comprising one or more air-permeable layers of molecular imprinted fabric, woven material, non-woven material, paper, polymer foam, woven fabric, knitted fabric, non-woven fabric, melt-blown fabric, ion-infused fabric, a non-fabric material, or a hydrophilic material to capture one or more airborne elements and/or one or more microdroplet-borne droplets to enable an interaction between one or more imprint cavities with one or more elements in the one or more airborne elements and/or the one or more microdroplet-borne droplets.

4. The filtering apparatus of claim 1 wherein the electronic enhancement comprises at least one of an interdigital electrode, a semiconductor, a nanoparticle quantum dot, a nano-island, a quantum wire, other nanostructured component, a sensor wire, a piezoelectric element, an acoustic waveguide, an optical waveguide, an optical fiber, an ultrasonic transducer, or a laser.

5. The filtering apparatus of claim 1, wherein the electronic enhancement performs at least one action comprising:
   generating a static and or time-varying electrical field;
   producing an electron wave function configuration that dynamically reconfigures at least a portion of an electron charge distribution within one or more imprinted cavities;
   enabling fine tuning of one or more imprinted cavities to enhance its response to a range of elements;
   generating at least one of ultrasonic or electromagnetic waves providing energy to free an element or elements from one or more imprinted cavities; or mechanically agitating an element or elements to induce interaction with or release from the imprinted cavity or re-activates a capture function of the imprinted cavity.

6. The filtering apparatus of claim 1 wherein the at least a portion of the electronic enhancement forms the substantially uniform filtering matrix region by interweaving with filtering material.

7. The filtering apparatus of claim 1 wherein detection by the electronic enhancement or by a sensor of at least one of a pathogen, contaminant, or other agent from the environment and/or from a user triggers at least one of an indicator or a treatment action.

8. A method for manufacture of an air filtration apparatus, the method comprising:
imprinting a protein, antigen, or other molecule binding site template by absorption of a relevant molecule or compound onto a silicate mineral or by other imprinting technique to create a polymer film or other imprinted film;
depositing the polymer or other imprinted film onto one or more layers of an air permeable material to create an imprinted material; and
integrating an electronic enhancement into fibers or other structure comprising the imprinted material to form a substantially uniform filtering matrix region for at least one layer of the air filtration apparatus.

9. The method of claim 8 wherein the electronic enhancement comprises at least one of an interdigital electrode, a semiconductor, a nanoparticle quantum dot, a nano-island, a quantum wire, other nanostructured component, a sensor wire, a piezoelectric element, an acoustic waveguide, an optical waveguide, an optical fiber, an ultrasonic transducer, or a laser.

10. The method of claim 8 further comprising configuring the air filtration apparatus as a face mask or other protection equipment.

11. The method of claim 8 wherein the step of integrating the electronic enhancement into fibers or other structure comprising the imprinted material to form a substantially uniform filtering matrix region for at least one layer of the air filtration apparatus comprises:
interweaving the electronic enhancement with imprinted material to form the substantially uniform filtering matrix region.

12. The method of claim 8 further comprising:
including a sensor for registering presence of at least one of a pathogen, contaminant, or other agent from an environment and/or from a user.

13. A filtering apparatus comprising:
an imprinted material comprising one or more imprints on at least a portion of the imprinted material to capture an element or elements; and
an electronic enhancement incorporated into a filtering region of at least one layer of the filtering apparatus, in which the filtering region comprises a matrix of the electronics enhancement and imprinted material.

14. The filtering apparatus of claim 13 wherein an element comprises a molecule or a compound.

15. The filtering apparatus of claim 13 wherein the imprinted material comprises imprints of at least two or more types of imprints for targeting different elements.

16. The filtering apparatus of claim 13 wherein the matrix comprises an interweaving of the electronic enhancement and imprinted material.

17. The filtering apparatus of claim 16 wherein the matrix forms a substantially uniform matrix of the electronic enhancement and imprinted material.

18. The filtering apparatus of claim 13 wherein the electronic enhancement or a sensor is used to detect presence of an element or elements.

19. The filtering apparatus of claim 17 further comprising an indicator for indicating detected presence of the element or elements above a threshold level.

20. The filtering apparatus of claim 17 further comprising a reservoir of an inhalable or medication that is triggered for release responsive to detected presence of the element or elements above a threshold level.

21. The filtering apparatus of claim 6, wherein the interweaving of the at least a portion of the electronic enhancement with filtering material comprises at least one of:
one or more comb-shaped interlocking arrays of electrodes;
a fan-shaped array of radially-oriented electrodes;
an array of concentrically-oriented circular electrodes;
one or more other configurations comprising electrodes; or
a combination thereof.

* * * * *